United States Patent [19]

Goodin et al.

[11] 4,404,069

[45] Sep. 13, 1983

[54] ELECTROLYTIC DESULFURIZATION OF ANILINO SULFUR COMPOUNDS

[75] Inventors: Richard D. Goodin, St. Louis; John P. Chupp, Kirkwood; Terry M. Balthazor, University City; James P. Coleman, Maryland Heights, all of Mo.

[73] Assignee: Monsanto Company, St. Louis, Mo.

[21] Appl. No.: 358,771

[22] Filed: Mar. 17, 1982

[51] Int. Cl.³ .......................... C25B 3/04; C07C 85/20
[52] U.S. Cl. .............................. 204/59 R; 204/73 R; 564/442; 564/102
[58] Field of Search ...................... 204/72, 73 R, 59 R

[56] References Cited

U.S. PATENT DOCUMENTS

| | | | |
|---|---|---|---|
| 3,461,172 | 8/1969 | Previc | 564/486 X |
| 3,480,525 | 11/1969 | Wessling et al. | 204/59 |
| 3,480,527 | 11/1969 | Wessling et al. | 204/73 R |
| 3,607,686 | 9/1971 | Buecheler | 204/73 R |
| 3,616,314 | 10/1971 | Settineri et al. | 204/59 |
| 4,072,584 | 2/1978 | Cipris et al. | 204/73 R |
| 4,209,464 | 6/1980 | Steinman et al. | 564/102 |
| 4,248,678 | 2/1981 | Goodin et al. | 204/59 R |

OTHER PUBLICATIONS

L. Horner and N. Neumann, Chem. Ber., 1965, 98, 1715
N. F. Loginova and V. N. Marianonskii, J. Gen. Chem. USSR, 1974, 44, 1805
V. G. Mairoanonskii, Angeu. Chem. Int. Ed. Engl., 1976, 15, 281.

Primary Examiner—F. Edmundson
Attorney, Agent, or Firm—Joseph D. Kennedy; James W. Williams, Jr.

[57] ABSTRACT

Various substituted ortho-alkyl anilines are prepared by electrolytic desulfurization of various benzyl sulfides, sulfoxides and sulfones, e.g. 2-methyl-6-trifluoromethylaniline is prepared from 2-amino-3-trifluoromethylbenzyl sulfides, sulfoxides and sulfones. The processes are conducted in concentrated aqueous quaternary ammonium hydroxide, as well as in aprotic media. The substituted anilines obtained are useful as intermediates for herbicide compounds.

17 Claims, No Drawings

ELECTROLYTIC DESULFURIZATION OF ANILINO SULFUR COMPOUNDS

The present invention is concerned with the electrolytic desulfurization of ortho-aminobenzyl sulfur compounds to obtain ortho-alkyl anilines, as by electrolytic desulfurization of ortho-aminobenzyl sulfides, sulfoxides and sulfones, and in particular such reactions of 3-tri-fluoromethyl-2-aminobenzyl sulfides, sulfoxides and sulfones to obtain 2-trifluoromethyl-6-methylaniline.

BACKGROUND OF THE INVENTION

The present invention involves use of electrolytic desulfurization procedures to prepare orthoalkyl anilines. Various chloroacetanilides, including those with orthoalkyl and perfluoroalkyl substituents, are known to be useful as herbicides or intermediates therefor. The present invention is concerned with preparation of particular types of compounds which are particularly useful and valuable as intermediates in preparation of herbicides, as further described herein with reference to patents of others, and to commonly assigned patent applications of one or more of the present applicants or their associates. Similarly, the sources of reactants are described with reference to published patents and commonly assigned applications. A number of publications have concerned the electrolytic cleavage of sulfide, sulfoxide or sulfone compounds. See L. Horner and N. Neumann, *Chem. Ber.*, 1975, 98, 1715; B. Lamm and K. Ankner, *Acta Chem. Scapd. B.* 1977, 31, 375; J. Y. Pape and J. Simonet, *Electrochim. Acta,* 1978, 23, 445; R. Gerdil, *J. Chem. Soc.* (B), 1968, 1071; V. G. Mairanovskii and N. F. Loginova, *J. Gen. Chem. USSR,* 1973, 43, 204; N. F. Loginova and V. G. Mairanovskii, *J. Gen. Chem. USSR,* 1974, 44, 1805; V. G. Mairanovskii, *Angew. Chem. Int. Ed. Engl.,* 1976, 15, 281. These publications for the most part are concerned with particular procedures, such as using anhydrous aprotic solvents, and do not involve compounds with ortho amino groups, or ortho trifluoromethylanilino groups. Compounds such as 2-methylthiomethyl-6-trifluoromethylaniline can be desulfurized by Raney nickel. However, the reaction uses a large excess of Raney nickel which adsorbs 25% or so of the product in virtually non-recoverable form. The pyrophoric nature of the reagent also makes its use unattractive.

SUMMARY OF THE INVENTION

The present invention involves the discovery that ortho-amiobenzyl sulfur compounds can be reductively cleaved by electrolysis to give the corresponding ortho-alkylanilines, in many cases with good selectivity, even though the amino group would be expected to make the compounds more resistant to discharge at the cathode. It has further been found that a trifluoromethyl substituent can be present and carried over into the product, even though such substituent is susceptible to cathodic reduction. In another aspect the invention involves conducting the process so that sufficient of the aminobenzyl sulfur compound is present in the electrolysis medium at the current density employed, so that it is reduced in the desired manner in preference to reduction of the product or other interfering reactions. Thus, in batch procedures, it is generally advantageous to stop the electrolysis short of complete conversion of the reactant, and it is further advantageous to use continuous procedures with continous or incremental addition of reactant and removal of product. It has further been found that both aprotic systems and aqueous systems can be used, the aqueous systems being suitable in conjunction with high concentrations of quaternary ammonium hydroxides to suppress hydrogen generation, and with the aqueous sytems having some advantages, particularly with regard to product extraction. With electrolysis in aprotic medium, it is advantageous to employ a cation-exchange membrane cell divider, and to permit hydrogen proton movement across it from anolyte to catholyte to prevent the catholyte from becoming progressively alkaline.

The present invention involves the conversion of ortho-aminobenzyl sulfur compounds, I, to orthoalkyl anilines, II

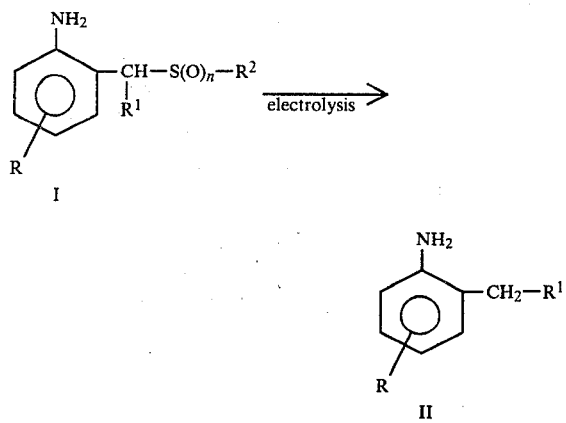

where
R equals alkyl, perfluoroalkyl or alkoxy
$R^1$ is H, alkyl or unsaturated alkyl
n equals 0-2
$R^2$ is alkyl or aryl;
A reaction of particular interest is:

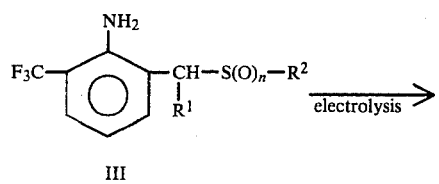

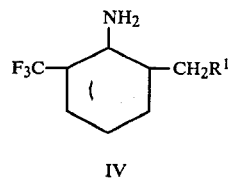

where $R^1$, $R^2$ and n have the same meanings as above.

In the anilinosulfur compounds illustrated as compounds I and III herein, the alkyl and other groups employed as R, $R^1$ and $R^2$ substituents can vary over a broad range of number of carbon atoms, e.g. from 1 to 10 or so carbon atoms, but more often in the range of 1 to 6 or so carbon atoms, e.g. methyl, ethyl, isopropyl, butyl, sec-butyl, amyl, hexyl, etc., and similarly for alkoxy, methoxy, butyloxy, etc. Various perfluoroalkyl groups can be present, but groups such as trifluoromethyl, pentafluoroethyl, etc. are lilkely to be of most interest. Ordinarily, there will be only one of the illustrated R substituents on a position of the aniline ring, but it is possible to have such substituents on additional positions and still obtain the desired reaction.

The R groups on the ring can be the same or different. The trifluoromethyl group is of particular interest as a substituent, and methyl, ethyl, methoxy and ethoxy substituents may also be particularly suitable for use. Some compounds of interest have the R group ortho to the amino group of the aniline, but the present process can be effected with an R substituent in the meta or para position.

The $R^1$ group on the $\alpha$ carbon of the sulfur-bearing moiety is preferably hydrogen, but alkyl or unsaturated alkyl groups can be employed, such as ethyl, methy, vinyl, or allyl. Some examples of reactants which can be employed in the present process include 2-methylsulfinylmethyl-6-trifluoromethylaniline, 2-methylthiomethyl-6-trifluofomethylaniline, 2-methoxy-6-methylthiomethylaniline, 2-methoxy-6-methylsulfinylmethylaniline, 2-methyl-6-methylthiomethylaniline, 2-methyl-6-methylsulfinylmethylaniline, 2-methoxy-6-methylsulfonylmethylaniline, 2-phenylsulfinylmethyl-6-trifluoromethylaniline, 2′methylsulfonyl(1-ethyl)-6′-trifluoromethylaniline. and 2-methylsulfinylmethyl-5-trifluoromethylaniline. In the process of the present invention the $R^2$ group in the illustrated formula does not appear in the product and various organic radicals can be employed, so long as they do not cleave more readily than the substituted benzyl group in the reactant. However, the methyl group is a simple group for use, and the methylthiomethyl and related sulfinyl and sulfonyl groups can be conveniently prepared by reactions illustrated herein, making the methyl group the usual choice. However, reactants with various other $R^2$ groups can be prepared and utilized if desired. While $R^1$ and $R^2$ will generally be hydrocarbyl, it will be recognized that non-interfering substituents can be present thereon, and that this is also true as to substituents elsewhere in the reactant.

The ortho-aminobenzyl sulfur compounds of the type I employed herein are indicated as known and to be useful in the preparation of sulfinyl indazoles, see Jackson U.S. Pat. Nos. 3,996,371 and 4,006,183. The compounds I can be prepared as described therein. The particular compound III can be prepared from ortho-aminobenzotrifluoride by oxidative condensation with dialkyl sulfide, e.g. dimethyl sulfide, using N-chlorosuccinimide as the oxidant. The resulting sulfilimine hydrochloride when neutralized for example, with triethylamine, may be thermally rearranged to obtain a compound III, particularly 2-methylthiomethyl-6-trifluoromethylaniline. The ortho-aminobenzotrifluoride is a known compound which can be prepared by the method of Reuben Jones, described in *Journ. Amer. Chem. Soc.*, Vol. 69, page 2346, (1947). Suitable procedures for preparing ortho-aminobenzotrifluoride are also described in West German OPI Application DE 3017542 and European Patent OPI Application EP 38-465.

The compounds produced in the present invention are in general known compounds with known uses, and have further been found by one of the present applicants and associates to have great value as intermediate compounds for preparation of particular classes of herbicides. Thus Krenzer U.S. Pat. No. 3,966,811 describes various compounds including compounds of the II and IV compound structures as useful intermediates for production of acetals of anilinoacetaldehydes which are useful as herbicides. U.K. patent application GB 2,013,188 and Swiss Pat. Nos. 579,348 and 585,191, which have been published, teach anilines, including compounds of structure II, as intermediates for herbicidally active chloroacetanilides. The compounds of types II and IV, particularly IV, have been found useful in preparation of particularly effective herbicides as described in a commonly assigned Belgian Pat. No. 887,997 which describes 2-haloacetanilides which are particularly effective against perennial weeds such as quackgrass and nutsedge in various crops, particularly corn and soybeans with the acetanilides being particularly exemplified by N-(ethoxymethyl)-2′-trifluoromethyl-6′-methyl-2-chloroacetanilide.

The compounds are particularly effective as preemergence herbicides, although post emergence activity has also been shown. The compounds II and IV above can be converted to chloroacetanilides by reaction in conventional manner with chloroacetyl chloride. For example, 2-methyl-6-trifluoromethylaniline is converted to 2′-methyl-6′-trifluoromethyl-2-chloroacetanilide. The chloroacetanilide is then reacted with chloromethyl ethyl ether in methylene chloride, utilizing benzyl triethylammonium bromide as a phase transfer catalyst, to obtain N-(ethoxymethyl)-2′methyl-6′-trifluoromethylchloroacetanilide. The preparations are further described in the aforesaid Belgian Pat. No. 887,997.

The present electrolysis process involves reducing the selected sulfide, sulfoxide or sulfone reactant at the cathode, and this occurs at a cathode voltage sufficiently negative to effect discharge of the reactant. The components of the reaction medium and conditions used will be suitable for the desired reactions. Thus it will generally be desirable to employ electrolytes with cations of very negative discharge potential, such as quaternary ammonium compounds. Various electrolysis mediums capable of dissolving the aniline reactant and passing an electric current can be used. It will be advantageous to use solvents which do not discharge at the cathode under the conditions employed, particularly at the cathode voltage required to discharge the aniline reactant. Aprotic solvents are generally suitable in this regard. It is preferable that the solvents be polar, e.g. dipolar solvents, as such solvents tend to have appreciable conductivity.

Examples of such suitable aprotic solvents include acetonitrile, propanenitrile, benzonitrile, dimethylformamide, other di-substituted amides such as dimethylacetamide, diethylformamide and dimethylpropioamide, dimethyl sulfoxide, cyclic ethers such as tetrahydrofuran and dioxane, etc. Ordinarily, it will be desirable that the solvent medium have a dielectric constant at least as high as 25. It is desirable that the solvent be capable of dissolving the aniline reactant, but solvents in whrich the reactant has limited solubility can be employed, in some cases forming an emulsion with the reactant. Protic solvents, such as water, can also be used, but under conditions where the desired reactant is reduced, and the current is not expended in simply generating hydrogen. Despite the propensity to cause hydrogen generation, water has advantages over other solvents in several respects. The propensity toward hydrogen generation can be lessened by use of high concentrations of quaternary ammonium compounds, especially of hydroxides, as the basicity appears to lessen the interfering discharge. Also, the aqueous media, it is advantageous to use high hydrogen overvoltage materials as cathode, such as mercury, lead, cadmium, zinc and the like. Mercury is especially suitable in this regard, although solid electrodes of lead or cadmium may be more convenient for use in some applications. The various aniline sulfides, sulfoxides and sulfones employed as reactants in the present process will vary somewhat in cathodic discharge potential, and in general, the less negative the discharge potential of a compound, the more easily it can be employed in an electrolysis with aqueous media. The sulfoxide compounds are usually more difficult to discharge than the sulfones, and the sulfides and more difficult than the sulfoxides. It follows that electrolysis in aqueous media tends to give better results with sulfoxides and sulfones than it does with sulfides.

A supporting electrolyte is generally used in the present process, being an electrolyte capable of carrying current but not discharging under the electrolysis conditions. With the present reaction of interest being at the cathode, the cation of the electrolyte is the significant ion in regard to avoiding interfering discharge, and quaternary ammonium ions are particularly suitable, although other cations of sufficiently negative discharge potential can be used. The term "quaternary ammonium" is employed herein to mean a cation with four organic groups substituted on a nitrogen, including those in which the nitrogen may be in a heterocyclic ring. Among the useful quaternary ammonium groups are tetraalkylammonium groups, such as tetramethyl-tetraethyl-, tetrapropyl-, and tetrabutylammonium groups, as well as those with different substituents, e.g. ethyltrimethylammonium, etc., and aralkylammonium groups, such as benzyltrimethylammonium and the like. The electrolyte can use various anions as the anionic component, such as halides, phosphates, hydroxide, perchlorates, etc. and these and other salts of the foregoing or other suitable cation can be used. The anion will often be selected with regard to the medium, as in using halides for organic media, while hydroxides can be used for aqueous media. Hydroxides, unless solvated by a complete solvation shell of water, are for the most part too reactive for efficient use in organic media, possibly catalyzing chemical reactions. Sulfates and aromatic sulfonates can be used, and may serve a useful hydrotropic function when both organic and aqueous components are present.

The use of acetonitrile and similar organic solvents is advantageous in that the reactants employed in the present process tend to be fairly soluble in such solvents. However, when used with moderate concentrations of quaternary ammonium salts, the water in the medium must be kept to fairly low concentrations, preferably near anhydrous, as the discharge of water at the cathode is an interfering reaction. It is true that some proton source is needed to complete the reaction in the catholyte, and this can be supplied by proton transport across the cell divider with the electric current. However, when an aqueous anolyte is used, water is transported with the proton, and this necessitates some means to dry the catholyte if electrolysis is to continue for an extended time. It would therefore be advantageous to modify the organic solvent electrolysis conditions to avoid need for aprotic conditions, possibly in a manner similar to that described herein for aqueous media.

The organic media are fairly good solvents for the products of the present process. While this may contribute to the convenience of the electrolysis itself, it tends to prevent use of simple extraction procedures for product separation.

In general the concentrations of the aniline sulfur reactant in aprotic solvents do not greatly affect the efficiency of the electrolysis. Thus very dilute solutions can be used, on up to very concentrated solutions which may be more convenient for large scale production. For example, from less than 1% by weight up to 30% or more by weight, or even 50% or so if such amounts are soluble. Ordinarily, it will be desirable to avoid exceeding solubility limitations, although emulsions can be used if desired. Thus, a suitable range may be from less than 1% up to the solubility limited in the particular solvent. In some cases, the quaternary ammonium salt may lessen solubility of the reactant, and it will be advisable to employ both the salt and reactant in concentration ranges to have both in solution. Also, product solubility is a factor, and consideration should be given to having a medium in which the product does not come out of solution, bringing reactant and salt with it. Thus, in some cases an amount of reactant well below its solubility limit may be used, in order to provide for product solubility as the reaction proceeds. Another approach is to extract the product with an appropriate solvent as the reaction proceeds. When aprotic catholyte is used, it is advantageous to employ a cation-exchange membrane cell divider, and to permit proton movement across it from an acidic anolyte.

Despite the highly negative discharge potentials required in the present process, it has been found that aqueous media can be used, in conjunction with high concentrations of quaternary ammonium hydroxides. Thus the concentrations of such hydroxides may be in the range of 5 or 10 to 50% or so by weight, or even higher, up to the limits of solubility or sufficient liquidity for practical operation. In aprotic media, the electrolyte concentrations are often much lower, as in the range of 0.05 molar to 0.5 molar, but considering the concentrations which may be useful in various media, they range from less than 0.05 molar to over 2 molar, or in terms of weight percent, from less than 2% to 30% or 40% or more, depending to some extent upon solubility and viscosity considerations. Fairly broad ranges are generally operable, but for aqueous systems there is advantage in the use of high concentrations of quaternary ammonium hydroxides. The quaternary ammonium hydroxide concentration will be high enough to keep hydrogen generation to acceptably low levels. Quaternary ammonium salts may be used along with the hydroxides.

The quaternary ammonium salts or hydroxides contribute to the solubility of the reactants, particularly in aqueous media, although this will vary with the concentration of the salt or hydroxide, and the particular salt, hydroxide and reactant involved. In the case of the amino-trifluoromethylbenzyl sulfur compounds, the sulfone and sulfoxide are more soluble in aqueous media than the sulfide. Thus with the sulfide, it may be necessary to use relatively low current densities to avoid current in excess of that needed to reduce the sulfide compound available in solution at the cathode surface. A broad range of current densities can be used to effect the present process, such as from less than 5 milliamperes/cm$^2$ to over 100 milliamperes/cm$^2$, but operations will more commonly be in the range of about 20 to about 80 milliamperes/cm$^2$, or better, about 50 to about 80 milliamperes/cm$^2$. The lower parts of the ranges are effective, but there is advantage in using relatively high density to produce more rapid reaction and efficient use of equipment. Of course, the maximum densities for effective use are affected by mass transfer rates, catholyte circulation or stirring, reactant solubility, etc. which determine the amount of reactant available at the cathode surface for reaction. With sulfide reactants of poor solubility in aqueous media, it may be appropriate to operate at current densities near 5 milliamperes/cm$^2$, or even lower, which would make the process unattractive economically. It appears that use of cosolvents or particular salts will improve solubility and make the use of such sulfides in aqueous media more attractive, for example, using a mixture of acetonitrile and water as utilized in Example 16 for a sulfone reactant. The current density can be regulated so as not to have current in excess of that needed to reduce the aniline sulfur compound available at the cathode. This can be monitored by chromatography, ascertaining that all of the current is accounted for in terms of reaction, i.e. disappearance of the aniline sulfur reactant, for which theory in the present process is 2 Faradays/mole (ignoring further reduction of cleavage product in some instances).

Good current efficiency can be obtained, but because of variations in flow rates, diffusion, etc. there will be instances where reactant is not available at particular points on the cathode, and other electrolysis reactions occur. However, it is generally possible to operate at current densities well removed from those that are excessive, so that very high or nearly quantitative current efficiencies are obtainable with respect to reactant disappearance.

The aqueous catholyte systems used herein may have organic co-solvents, as well as water. Solvents which are useful as aprotic solvents, but possess water miscibility over useful concentration ranges, can be used, especially if they contribute to solubility of reactants of interest. Such systems have the characteristics of those herein using water as solvent, in that water is present along with large amounts of quaternary ammonium hydroxides to supress the tendency to hydrogen generation. The amount of water is sufficient to serve as a solubilizing medium for the hydroxides.

In reactions conducted in aprotic solvent, particularly in the reaction of 2-methylthiomethyl-6-trifluoromethylaniline, the reaction can be conducted in a batch procedure with fairly good selectivity to the desired aniline product up to 85 to 90% conversion of the starting aniline sulfur reactant. As the reaction is continued beyond such conversions, there is an increasing tendency to reduce the trifluoromethyl derivative, producing difluoromethyl derivatives of the product, and to some extent of the starting reactant. Thus selectivity can be enhanced by stopping the reaction before conversions exceed 85 to 90% or so. Aside from conversions, it will be desirable not to operate at steady state or for extended times with product in excess of reactant by more than a 9 to 1 ratio. For any particular procedure, the process can be stopped, concentrations adjusted, or product removed, if monitoring indicates substantial conversion to difluorocompounds.

In aqueous catholyte systems, consideration must still be given to avoiding reduction of the trifluoro group, being of particular interest for electrolysis of the sulfoxide containing compounds. Thus if the product concentration is too high in relation to the reactant, reduction of the trifluoro group will occur. Since extraction from the aqueous systems has been found feasible, the electrolysis can be continuous and the product can be extracted during the electrolysis, as additional reactant is added, thereby keeping the product at suitably low concentration, particularly with respect to the reactant. It happens that methylsulfinylmethyl-trifluoromethyl aniline is soluble in aqueous quaternary ammonium hydroxide systems to an amount of about 25% by weight, so electrolyses could be run with concentrations from less than 1 to 25% or so by weight. However, the resulting aniline product has poor solubility and tends to cause the reactant and quaternary ammonium compound to phase out of the electrolysis medium. For this reason it has been found convenient to use lower concentrations of the sulfoxide reactant, such as less than 10%, and often less than 5% by weight, and to continuously extract product, so that the product is not present in ratio to the reactant to invite further reduction. In fact, the extraction can keep the amount of product less than that of the reactant, often less than 1% of the electrolysis mixture and only a fraction of the amount of the reactant.

For continuous extraction, it is desirable to extract product with only minimal extraction of reactant. In the case of the sulfoxide and sulfone reactants, i.e. trifluoromethylbenzyl methyl sulfoxides and sulfones, the reactants are not soluble in n-pentane and it extracts the aniline product readily in preference to the reactants. Other hydrocarbon solvents can be used similarly, such as those alkanes from 5 to 8 or so carbon atoms, including both normal and branched-chain alkanes, as well as cyclic alkanes such as cyclohexane. Alkanes above octane will be less desirable, and also less convenient for use because of higher boiling points. Diethyl ether is also a good solvent for the products, but extracts the reactants as well, making its use more appropriate for batch reactions.

In the case of sulfone-containing reactants, there is not much tendency to reduction of trifluoromethyl groups in reactant or product compounds. The desulfurization reaction leaves conditions which are capable of utilizing the electric current, apparently in preference to the trifluoromethyl group. This to some extent mitigates against complete conversion of reactant. Also, in aqueous systems, the product tends to come out of solution, causing some of the quaternary ammonium compound to precipitate with resulting side reactions or inhibition of the desired reaction. Accordingly, it is desirable to use continuous extraction during an electrolysis, to remove product and keep the product at acceptable low levels, in a manner similar to that for electrolysis of sulfoxide-containing reactants. However, the reaction for sulfones differs in a significant respect from that for sulfoxides. The sulfoxide cleavage product is sulfenic acid, $CH_3SOH$, which is further reduced to methanethiol, and vented from the system. The sulfone cleavage product is sulfinic acid, $CH_3SO_2H$, and it is not ordinarily reduced further. If sulfinic acid is allowed to build up in a continuous process, it lowers the pH of the catholyte and eventually interferes with the electrolysis. For this reason, sulfoxide reactants appear more attractive for use in continuous processes than sulfone compounds, although sulfones are very suitable for batch reactions. Anion exchange membranes are available which are capable of passing the sulfinic anion from the catholyte to the anolyte and some progress has been made in using this as a way of avoiding sulfinic acid accumulation, making the electrolysis of the sulfone reactant more attractive for continuous electrolysis processes. For electrolysis of the methylsulfinylmethyltrifluoromethylaniline, n-hexane has been found suitable for use as a solvent for a continuous extraction, and other alkanes can also be used as described hereinabove.

In the present procedures it is advisable to use a divided electrolysis cell. The reactions can be conducted in an undivided cell, but anilines are susceptible to anodic oxidation, and it is difficult to avoid interference or loss of reactant in an undivided cell. For electrolysis in an aprotic medium, any of the generally useful electrode materials can be used as the cathode, including metals, alloys, graphite or other carbon electrodes, etc. known to the art. There may be advantage in using high hydrogen overvoltage materials, such as mercury, zinc, lead, cadmium and the like, and there is definite advantage in such use when aqueous media are employed as catholyte. The anode will not ordinarily have much influence on the reaction occurring at the cathode, so in general any suitable anode materials can be used. For long term usage, it will be advisable to use anodes which are reasonably stable under the electrolysis conditions. Platinum or platinum plated materials can be used, and carbon and lead are also suitable. Also de Nora-type dimensionally stable anodes, being anodes with precious metal oxides plated on a titanium substrate may be used. Such anodes are available from the Diamond Shamrock Company, Cleveland, Ohio. 44114.

The temperature at which the present electrolysis is conducted is not generally an important parameter, and ambient temperatures or lower, on up to about 100° C. or the boiling point of components can be used or higher if pressure is employed. The electrolysis may generate heat from electrical resistance, making it convenient to operate at somewhat elevated temperatures. In some cases slightly elevated temperatures may be advantageous in promoting solubility. There is ordinarily no need for elevated temperatures, and in some electrolyses high temperatures may tend to promote chemical reactions at the expense of the desired electrolysis reaction. Various general considerations concerning electrolysis in concentrated quaternary ammonium hydroxide can be found in U.S. Pat. No. 4,187,156 of one of the present applicants, James P. Coleman, and John H. Wagenknecht.

Ease of the electrolytic desulfurization of the benzyl sulfur compounds herein will vary somewhat with the substituents on the benzene ring of the compounds. Thus amino groups are electron donating and tend to make the sulfur moieties more resistant to electrolytic reduction, as shown by more negative cathode discharge potential. Alkoxy groups are also electron donating and increase resistance to reduction, but generally to a lesser extent than amino groups. Alkyl groups, like the methyl group, are electron donating but having a lesser effect on resistance than alkoxy groups. The discharge potential also varies with the sulfur group. Thus cyclic voltammetry was used to measure potential with several o-trifluoromethylaniline sulfur derivatives. At a heavy metal dimensionally stable electrode, such derivatives with an orthothiomethyl substituent give a shoulder at −2.8 volts; addition of an ortho-methylsulfinylmethyl substituted derivative gives a sharper shoulder at −2.65 volts; then addition of a methylsulfonyl-methyl substituted derivative gives a peak at −2.6 volts. Thus the voltages for the groups are in the order, $S > SO > SO_2$ The determinations were made in acetonitrile containing tetrabutylammonium perchlorate.

In some of the electrolyses herein a weak proton donor, such as phenol, is provided to supply proton needed for the reaction. Various other ways can be used to supply such proton, preventing development of excessive alkalinity, but the effect should be sufficiently weak as to avoid causing undue generation of hydrogen by discharge at the cathode. Phenol is suitable in this regard. Of course, this mainly concerns effects upon extended operations, and other measures can be used to counter or neutralize the alkalinity, or catholyte can be purged and replaced with new catholyte. In aqueous media, water provides proton for the reaction.

With respect to having an aqueous catholyte with appreciable solubility for reactants, and still having a system for efficient extraction of product, it has been found that a combination of acetonitrile and water makes a good catholyte medium with increased solubilizing ability over water. Moreover, it has been found that alkanes are good extracting solvents for removing the desired aniline products, e.g. methyltrifluoromethylaniline and ethyltrifluoromethylaniline, from such media, as alkanes of 5 to 8 or so carbon atoms, particularly pentane and hexane, are good solvents for such products and are immiscible with both water and acetonitrile.

EXAMPLE 1

A plate and frame cell was employed for a number of electrolyses, with electrodes having a nominal area of 350 cm$^2$. The cathode material was a cadmium sheet, while the anode was a platinum-coated titanium, or a lead sheet in some cases. A reinforced cation exchange membrane was employed as cell-divider, namely a polytetrafluoroethylene based sulfonic acid resin, Nafion ® 427 cation-exchange membrane. The electrode membrane gaps were 3 mm, and a polypropylene mesh prevented membrane-electrode contact and served as a flow disperser for the catholyte and anolyte being pumped through the electrode-membrane gaps. An aqueous 10% sulfuric acid solution was employed as anolyte. The catholyte was anhydrous acetonitrile with a 0.1 molar concentration of tetrabutylammonium bromide, with an initial 20% (weight/volume) concentration of a benzylsulfide reactant. The anolyte reservoir was a 1-liter flask, with approximately 500 ml. anolyte being used, and the catholyte reservoir was a 2-liter flask with approximately 1000 ml of catholyte being used. The catholyte cell exit stream entered a hydrocyclone gas-disengager which was purged with nitrogen, to remove methanethiol formed in the electrolysis. The catholyte circulation stream was also routed through a molecular sieve column to remove water, as water was transported across the cation exchange membrane with hydrogen ion during the electrolysis. The transported proton prevents the catholyte from becoming progressively basic during the reaction, which might promote side reactions. A number of batch runs were carried out in the cell, converting 2-methylthiomethyl-6-trifluoromethyl aniline to methyltrifluoromethylaniline, starting with a 20% concentration of the reactant, and adding additional reactant in increments during the course of the electrolysis to maintain an appreciable concentration, till a total of 200 grams had been provided for reaction. The cell was operated at a constant current of 10 amperes (28 milliamperes/cm$^2$) with a cell voltage of 6–7 volts. The electrolysis was continued till 85–90% conversion of the methylthiomethyl-trifluoromethylaniline. The current efficiency to 2-methyl-6-trifluoromethylaniline was typically 65–80%. Product was identified by gas chromatography and nuclear magnetic resonance. In some cases, the course of the reaction was monitored by gas chromatography. The trifluoromethyl group is subject to reduction at the cathode if the electrolysis is continued till little reactant is present, as by exceeding 90% or so conversion, and having a high product concentration, but little of the starting reactant. The trifluoromethyl group in the product is particularly subject to reduction to a difluoromethyl group if the concentration of reactant is undesirably low, and the group in the reactant is subject to such reduction to a lesser extent. The product was isolated by removal of acetonitrile under reduced pressure and extraction with ethyl ether to precipitate the tetrabutylammonium bromide salt. The ether extract was distilled at 69°–71° C./6 mm Hg.

EXAMPLE 2

An electrolysis was conducted in the cell and under general conditions of Example 1, employing a lead cathode and platinum plated anode. A different cation exchange membrane was used. The catholyte had 20 grams tetrabutylammonium bromide in 1 liter of acetonitrile and contained 50 grams of 2-methylthiomethyl-6-trifluoromethylaniline. The current was 5 amperes, at 6 volts. No cathode gassing was observed initially. After 2.16 hours, some gassing was noted and gas chromatrography indicated appreciable by-product formation. The voltage was then controlled, first to 5.5. volts, then to 5 volts, with current dropping to 3 amperes shortly after three hours, and then to 1.6 amperes, with the electrolysis being terminated at 3.5 hours after passage of 57,558 coulombs of 2.6 Faradays/mol of reactant, compared to 2 Faradays theory. After distillation of the acetonitrile and extraction, a 34.22 gram residue was obtained for an 87% recovery. Gas chromatography and NMR showed the major product to be 2-methyl-6-trifluoromethylaniline with a small amount of by-product and some starting reactant.

EXAMPLE 3

An electrolysis was run as in Example 1, employing a lead cathode, but alumina was used as a desiccant in place of the molecular sieve. A 34.43 gram amount of 2-methylthiomethyl-6-trifluoromethylaniline was employed in the 1 liter catholyte, and electrolysis was conducted at a 5 ampere current. Monitoring by gas chromatography showed nearly a linear increase in desulfurized product up to approximately 2 Faradays/mol reactant, with peaking at about 2.5 Faradays/mol with about 10% of the starting reactant remaining. Some difluoromethyl material began to appear at approximately 1.7 Faradays/mol. Electrolysis was continued to cause further conversion to difluoromethyl product. After passage of 5.8 Faradays/mol, the amount of difluoromethylmethylaniline was about 70%, compared to about 30% methyltrifluoromethylaniline, and almost no starting reactant. The gassing in this procedure with alumina desiccant appeared less than with a molecular sieve, but increased in the later stages of the reaction. After removal of acetonitrile by distillation, and ether extraction followed by aqueous washes, a 19.86 gram residue was obtained. Upon distillation, a small amount of product was obtained at 67°/5.3 mm Hg, but decomposition then began with some solid formation. HF from decomposition of the difluoro by-product forms a salt with distillate, as well as catalyzing further decomposition.

EXAMPLE 4

A run similar to Example 1 was made, but with tetrabutylammonium iodide in 1.2 liters acetonitrle, and with a cadmium electrode. Alumina was used as desiccant. A 44.8 gram amount of reactant was charged, and the electrolysis was continued to approximately 2 Faradays/mol reactant. Monitoring by gas chromatography showed smooth conversion to methyltrifluoromethylaniline, although some difluoromethyl compounds were observed. Two overnight extractions of the electrolysis mixture with n-pentane gave a total extract of 23.67 grams (compared to 35.5 grams theory for the intended desulfurized product).

EXAMPLE 5

In a small H-cell with cathode and anode chambers separated by a glass frit, a catholyte was provided with 3.5 grams tetrabutylammonium perchlorate in 125 ml dimethylformamide and a 0.642 gram amount of 2-methylthiomethyl-6-trifluoromethylaniline. A 0.56 gram amount of phenol was also present in the catholyte to provide proton for the reaction. The cathode was mercury, and the anode was carbon. The anolyte was a solution of tetrabutyl ammonium perchlorate in dimethyl formamide. The cathode voltage was −2.8 before phenol addition, and showed a double peak at −2.7 and −2.84 volts after phenol addition. Electrolysis was started at about 70 milliamperes current and varied from 85 milliamperes to 50 milliamperes, at varying voltages, till 620 coulombs had passed (compared to 560 theory for 2 Faradays/mol). Gas chromatography showed mostly the desired methyltrifluoromethylaniline, although some of the starting sulfide was present. The dimethylformamide was stripped off, and successive extractions and removals of ether and carbon tetrachloride, followed by ether treatment and H$_2$O washings, provided a 0.3 gram amount of product which was identified by NMR as fairly pure 2-methyl-6-trifluoromethylaniline.

EXAMPLE 6

An electrolysis was conducted as in Example 5, but employing a Nafion ® 427 cation-exchange membrane as a cell divider, and utilizing acetonitrile and tetrabutyl ammonium iodide as the catholyte medium, and the same medium in the anolyte, but containing a small amount of toluenesulfonic acid, to provide proton for transport across the membrane to the catholyte to counter alkalinity developed by the reaction in the catholyte. The anode reaction converted iodide ion to iodine. The cathode voltage from the sulfide reactant was −2.7 to −2.8 volts (vs. saturated calomel electrode). The potential was controlled to maintain a 200 milliampere current. Gas chromatography showed formation of methyltrifluoromethylanaline, with 90% conversion after passage of slightly over 2 Faradays per mole of reactant.

EXAMPLE 7

An electrolysis was conducted in a divided flow cell with lead cathode and anode and a Nafion ® cation exchange membrane divider. The sulfide reactant was 2-methoxy-6-methylthiomethylaniline, with a 100 gram amount provided in the catholyte containing 20 grams tetrabutylammonium bromide in 1 liter acetonitrile. The anolyte was 10% sulfuric acid. The catholyte flow was approximately 300 ml/minute, and the anolyte, approximately 200 ml/minute, and the circulating catholyte passed through a molecular sieve column. Area of the electrodes was 100 cm$^2$. A 6.4 volt cell potential gave a 5 ampere current. Earlier measurement had shown a cathode voltage of −3.2 volts (vs. Ag/AgCl electrode) for a solution of the methoxy reactant. Cathode gassing was apparent after 1.5 hours and continued during the electrolysis. After three hours, little change was noted in the product/reactant ratio. The electrolysis was stopped after 4 hours, short of the 5.8 hours needed for 2 Faradays/mole. Ether extraction and aqueous washings resulted in isolation at 80.85 grams material, which gas chromatography indicated to be 45%. 2-methoxy-6-methylaniline. NMR indicated 36% of the stated compound in the product.

The recovered material was used in a further electrolysis, resulting in a 74% conversion to the methoxymethylaniline.

EXAMPLE 8

An electrolysis was conducted with 2-methyl-6-methylthiomethylaniline as reactant, employing a flow cell as in Examples 1 and 2. A lead cathode and platinum anode were used. The catholyte was 30 grams of tetrabutylammonium bromide in 1 liter acetonitrile, and a 54.53 gram amount of the aniline was employed. Alumina was used as a dessicant in the catholyte stream. The electrolysis was conducted at 5 amperes. After 2.5 hours there was severe cathode gassing and the electrolysis was terminated. Extractions with ether and water were employed for product separation, and NMR and gas chromatographic analysis indicated 44–45% conversion to 2,6-dimethylaniline. Distillation gave a nominal fraction at 47° C./0.65 mm Hg, which was mostly 2,6-dimethylaniline; an 11.33 gram fraction at 46°/0.5 mm to 58°/0.33 mm, which was 92% 2,6-dimethylaniline and 7% o-toluidine, and a 24.69 gram fraction at 81°–87° C./0.20 mm which was 17% 2,6-dimethylaniline and 83% the starting sulfide reactant.

EXAMPLE 9

A cell was constructed from two polypropylene blocks with rectangular cavities forming an upper anolyte and lower catholyte chambers separated by a Nafion ® 120 cation-exchange membrane. The chambers were 6 inches wide by 34 inches long, 1416 cm$^2$ in area. The cathode was the surface of a 0.5 inch deep mercury pool, with a mercury to membrane gap of 0.75 inch. The anode was a dimensionally stable heavy metal electrode (DSA by Diamond Shamrock), and the gap to the membrane was 0.375 inch. A polypropylene spacer prevented membrane-anode contact.

There were provisions for circulating the catholyte and anolyte continuously from reservoirs through the cell, with return to the reservoir. An electrolysis was conducted in the cell to desulfurize 2-amino-3-trifluoromethylbenzyl methyl sulfoxide. In a continuous electrolysis, a 1 normal aqueous solution of 1,6-bis(-dibutylethylammonium) hexane hydroxide was employed as catholyte, with an average concentration of about 3% of the sulfoxide reactant. With continuous product removal, the product concentration in the catholyte averaged about 0.25%. The catholyte system used about 40 liters catholyte. The linear flow velocity across the cathode was about 4.5 inches/second, and that across the anode was about 3 inches/second. Current to the cell was 100 amperes, for a 76 milliampere/cm$^2$ density. The cell was operated under nitrogen, and a continuous side stream of catholyte was circulated through a filter to remove solids. The anolyte was 5% sulfuric acid. Water passed from anolyte to catholyte with protons, and catholyte concentration was maintained by concentrating a catholyte purge, by evaporation, and returning it to the cell. The sulfoxide reactant concentration was maintained by adding 500 grams of the compound dissolved in 3500 ml of hot catholyte solution to the system at two hour intervals. Product separation was accomplished by countercurrent extraction with cyclohexane in a column packed with berl saddles. A side stream of catholyte was fed to the top of the column. Cyclohexane exited the top of the column to an evaporation tank where cyclohexane was evaporated for recycle. Product in the evaporator was removed periodically and subjected to additional evaporation at reduced pressure. The electrolysis was operated successfully over a period of many hours, producing many kilograms of 2-methyl-6-trifluoromethylaniline purified by distillation. An appreciable amount of the sulfoxide reactant was recovered from still bottoms. The chemical yield of purified product approached 50%. However, this did not take into account the sulfoxide recovered from still bottoms, or some less pure product recovered from distillations. The cyclohexane used in the extraction removed some of the sulfoxide compound from the catholyte, along with the product. Also, some catholyte was on occasion discharged from the system and replaced with fresh catholyte, in order to remove solid or other contaminants with an unascertained loss of sulfoxide reactant. In some comparable laboratory electrolysis procedures, the chemical yield of purified methyltrifluoromethylaniline was better than 60%.

EXAMPLE 10

Electrolysis of 2-methylsulfonylmethyl-6-trifluoromethylaniline, 20 grams, in 200 ml of 1 molar tetrabutylammonium hydroxide was conducted in an electrolysis cell with a cadmium cathode. Conversion was very slow, so after 0.66 hours, a lead cathode was substituted. After an additional 2.66 hours, the total conversion to 2-methyl-6-trifluoromethyl aniline was about 23%.

EXAMPLE 11

A small electrolysis cell with Nafion ® cation-exchange membrane divider was utilized with a mercury cathode and platinum anode. The catholyte was 200 ml of 1 normal tetrabutylammonium hydroxide containing 20 grams of 2-methylsulfinylmethyl-6-trifluoromethylaniline and the anolyte was 100 ml of 10% by weight sulfuric acid. The cathode area approximated 24 cm$^2$. Electrolysis was conducted at a 1 ampere current for 6.75 hours. The conversion as monitored rose gradually from 17.6% methyltrifluoromethylaniline at 0.75 hours to 91.6% at 6.75 hours, when 2.98 Faradays had passed. The electrolysis mixture was extracted twice with 100 ml portions of pentane and, after drying over Mg SO$_4$, the pentane was stripped from the extracts, leaving 10.48 grams residue, which NMR indicated to be 10.09 grams of methyltrifluoromethylaniline. A 9.77 gram portion of the product was distilled, with 8.2 grams distillate being obtained.

EXAMPLE 12

The catholyte from Example 11, from which product had been extracted, was employed in a further electrolysis, but with a cadmium cathode. The cadmium electrode was about 25 cm² in area. A pump was used to cycle the catholyte through the catholyte chamber past the cathode, as a method of achieving better mass transfer than by stirring. At a 10–11 volt cell potential, 1 ampere current, the percent of methyltrifluoromethylaniline product increased from 8 to 41.8 over a 4-hour period, as shown by gas chromatography. The catholyte was extracted with pentane, and 4.28 gram product obtained, identified as 98.5% 2-methyl-6-trifluoromethylaniline by gas chromatography.

EXAMPLE 13

An electrolysis was conducted in a small divided H-Cell with mercury cathode and platinum gauze anode, employing 200 ml 1 normal tetrabutylammonium hydroxide as catholyte and 100 ml 10% sulfuric acid as anolyte. A 12.6 gram amount of 2-methylthiomethyl-6-trifluoromethylaniline was added to the catholyte and electrolysis conducted at 1 ampere (41.7 milliamperes/cm²). The catholyte was cycled through the cell by pumping to maintain an emulsion. After passage of 3 Faradays/mol, the electrolysis was terminated. Ether extraction and aqueous washing was used to isolate product, with 9.95 grams of material being obtained. Gas chromatography showed the desired methyltrifluoromethylaniline, along with difluoromethyl compounds. NMR confirmed presence of about 20% difluoromethyl compounds.

EXAMPLE 14

For electrolysis in a divided electrolysis cell at a mercury cathode, a 200 ml catholyte of 1,6-bis(dibutylethylammonium)hexane hydroxide and 10 grams 2-methylsulfinylmethyl-6-trifluoromethylaniline was provided. The bis-quaternary ammonium hydroxide portion had titrated at 252 milliequivalents/kg. The aniline compound present at 5% (weight/volume) did not dissolve, so the solution was made 0.4 molar with tetrabutylammonium bromide, effecting solution. Electrolysis was conducted at 1 ampere for 3.5 hours to effect 92.9% conversion. Pentane extraction produced 6.82 grams product, which was indicated by gas chromatography to be pure 2-methyl-6-trifluoromethylaniline.

EXAMPLE 15

Electrolysis was conducted as in Example 14, but the sulfoxide was dissolved by gentle warming, and no bromide salt was added. Chromatographic monitoring showed comparable conversion to the 2-methyl-6-trifluoromethylaniline.

EXAMPLE 16

An electrolysis was conducted to convert 2'-methylsulfonyl(1-ethyl)-6'-trifluoromethylaniline to 2-ethyl-6-trifluoromethylaniline. The electrolysis was conducted in a cell adapted for incremental addition of the reactant during the electrolysis, with extraction of product during the electrolysis. The initial charge was 125 grams of the reactant compound in 3 liters of an electrolyte which was a 50/50 weight mixture of acetonitrile and an aqueous solution of 1,6-bis(dibutylethylammonium) hexane hydroxide. Electrolysis was conducted at currents of 10–20 amperes in a series of electrolytic procedures, with addition of about 50–100 grams additional reactant each hour, as needed to maintain a reactant concentration of about 125 grams for 3 liters. The aqueous solution used as part of the catholyte contained from about 600 to 1000 milliequivalents per liter of the specified quaternary ammonium hydroxide, with the actual strength varying for different procedures, but apparently without affecting results significantly. In the electrolyses, the addition of reactant generally occurred over about 5 hours, which was followed by an additional 4 hours or so reaction period with some variation depending upon the current utilized and process parameters monitored. The total reactant in each electrolysis run was 350 to 400 grams. Toward the end of an electrolysis run it was evident that there was a build-up of methanesulfinic acid to gradually neutralize the catholyte, and there was gassing at the cathode. The sulfone reactant had solubility in the catholyte close to 5% by weight, and approximately a 4% concentration was used during an electrolysis run. Toward the end of a typical electrolysis the sulfone reactant concentration had declined to about 0.4%, while the product had been removed to an extent that its concentration was about 0.2%. The product was removed by continuous counter-current extraction of a catholyte stream with n-hexane. There was some build-up of difluoro compounds, as the hexane was somewhat selective for the desired product over the difluoro compounds. In a series of electrolysis runs generally as described in this example, a total of 5025 grams was processed, and the extracted product combined for distillation. The distillation yielded 2250 grams of 2-ethyl-6-trifluoromethylaniline of 98% purity. The 2250 grams calculates as a 63% chemical yield. The distillation left a large amount of still bottoms, which may have contained starting sulfone compound and difluoromethyl compounds. The electrolysis cell used in these runs was fabricated from parts including a cylindrical glass container about 25.4 cm in diameter having a 1 cm deep mercury pool on the bottom as a cathode (450 cm²), with an insulated copper electrical connection. A 17.8 cm glass tube, with bottom fitted with a Nafion ® 427 cation exchange membrane served as the anode compartment. The tube was equipped with a flange at the bottom, and nylon bolts through the flange supported the anode chamber about 1.0 to 1.5 cm above the cathode surface. An expanded metal DSA (dimensionally stable anode, Electrode Corporation TIR-2000), 16.5 cm in diameter was mounted horizontally above the membrane. A catholyte circulation system terminated with a sprinkler head disperser in the middle of the mercury pool, providing radial mass transfer across the cathode surface. A portion of the catholyte was circulated to the top of a packed column for hexane extraction of product, with return of catholyte to the cell. The hexane was continuously distilled from a reboiler pot and entered the column under gravity feed at the bottom, overflowing from the top to return to the reboiler pot. A current of 20 amperes (45 milliamperes/cm²) required a cell voltage of about 5–8 volts.

The 2'-[methylsulfonyl(1-ethyl)]-6'-(trifluoromethyl) aniline for use as reactant in Example 16 can be obtained by treating 2-methylthiomethyl-6-trifluoromethylaniline with 40% peracetic acid, to oxidize the sulfide group to a sulfonyl group and also oxidizing the amino group to a nitro group, reacting the resulting compound with dimethylsulfate, using benzylthioethylammonium chloride as a phase transfer catalyst with 50% NaOH, and then hydrogenating to reduce the nitro group and obtain the desired 2'-[methylsulfonyl(1-ethyl)]-6'-(trifluoromethyl)aniline. This process is the invention of the applicants of commonly assigned copending U.S. application Ser. No. 358,774, filed of even date herewith, and is described in more detail in that application. If desired, the nitro group can be reduced at the cathode as a prelude to the electrolysis of the resulting aniline.

EXAMPLE 17

A glass H cell with a glass frit divider had an Hg cathode (3 cm diameter) and carbon rod anode. A 50 ml amount of 1 normal tetrabutylammonium hydroxide in water was used as electrolyte, with about 30 ml. being in the cathode chamber. A 5 gram amount of 2-methylthiomethyl-6-trifluoromethylaniline was added to the catholyte. The materials were immiscible, but were mixed by mechanical stirring. The cell was warmed to about 40° C. and electrolysis was conducted at a 500 milliampere current. Gas chromatography showed decline in the amount of starting reactant and production of 2-methyl-6-trifluoromethylaniline, and after 2.5 hours a large amount of material had reacted with the major product being 2-methyl-6-trifluoromethylaniline. In a similar procedure, a smaller cell was used with a 3.81 by 2.54 cm lead cathode and employing 1 gram of the methylthiomethyltrifluoromethylaniline in 25 ml of the tetrabutylammonium hydroxide solution at 100 milliamperes. After 45 minutes, 2-methyl-6-trifluoromethylaniline was produced, but the amount was very small compared to the previous results.

EXAMPLE 18

An electrolysis was conducted similarly to the first procedure in Example 17 but employing an undivided cell formed from a resin pot with a Hg pool cathode and a small stainless steel coil as anode. Electrolysis was conducted at 50° C. and 1 ampere. Results were similar to those in the first electrolysis of Example 17, with methyltrifluoromethylanaline being the major product. With addition of an additional 10 grams of the reactant and continued electrolysis, the catholyte solution gradually turned dark brown but the product results were still comparable to those of Example 16 when the electrolysis was terminated at four hours.

EXAMPLE 19

An H-cell was fitted with an anion-exchange membrane (Raipore R-5035). The catholyte was 200 ML of 20% 1 M tetrabutylammonium hydroxide in acetonitrile containing 7,5 g of 2'-methylsulfonyl(1-ethyl)-6-trifluoromethylaniline and the cathode was a Hg pool. The anolyte was 10% sulfuric acid and the anode was a platinum wire mesh. The electrolysis was run at a constant current of one amp. During the 6-hr electrolysis, an additional total of 12.5 g of sulfone reactant was added at intervals.

Monitoring by liquid chromatography showed a smooth conversion to desired 2-ethyl-6-trifluoromethylaniline. After 6 hours, the pH had not significantly decreased, indicating little build-up of methylsulfinic acid in the catholyte. Extraction with hexane gave a product which was pure 2-ethyl-6-trifluoromethylaniline by NMR analysis.

The anilino sulfoxide compounds used herein for desulfurization to o-alkylanilines can be readily prepared by oxidation of the corresponding anilino sulfides, as by oxidation with hydrogen peroxide. Thus 2-methylthiomethyl-6-trifluoromethylaniline is treated with hydrogen peroxide catalyzed by acetic acid to convert it to 2-methylsulfinylmethyl-6-trifluoromethylaniline. Such procedures have been further described in commonly assigned copending U.S. application Ser. No. 358,956, filed of even date herewith.

What is claimed is:

1. A process of preparing ortho-alkylanilines which comprises electrolyzing at a cathode an orthoaminobenzyl sulfide, sulfoxide, or sulfone at a cathode potential sufficiently negative to effect reductive cleavage of the sulfur-containing moiety from the benzyl moiety producing an ortho-alkyl aniline.

2. The process of claim 1 in which the named reactants have a trifluoromethyl substituent adjacent to the amino group on the benzyl ring.

3. The process of claim 1 in which the reaction is represented by:

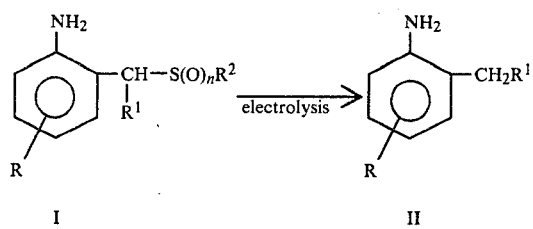

where
R equals alkyl, perfluoroalkyl or alkoxy
$R^1$ is H, alkyl or unsaturated alkyl
n equals 0–2
$R^2$ is alkyl or aryl.

4. The process of claim 1 in which the reaction is represented by:

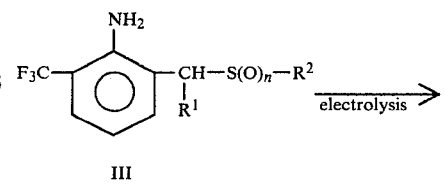

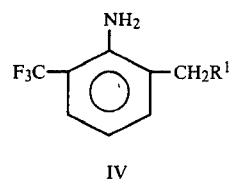

where $R^1$, $R^2$ and n have the same meaning as in claim 3.

5. The process of claim 1 in which a reactant compound selected from 2-methylthiomethyl-6-trifluoromethylaniline, 2-methylsulfinylmethyl-6-trifluoromethylaniline and 2-methylsulfonylmethyltrifluoromethylaniline is converted to 2-methyl-6-trifluoromethylaniline.

6. The process of claim 1 in which the electrolysis is carried out in an aprotic medium in the presence of quaternary ammonium cations.

7. The process of claim 1 in which the electrolysis is carried out in an aqueous medium with a high concentration of quaternary ammonium hydroxide to suppress hydrogen formation.

8. The process of claim 1 in which the electrolysis is stopped before conversion has exceeded 90%, in order to lessen side reactions.

9. The process of claim 1 in which product is removed during the electrolysis by extraction with a solvent from catholyte with return of catholyte to the reaction.

10. The process of claim 9 in which the solvent is a liquid lower alkane.

11. The process of claim 5 in which electrolysis is effected in an aqueous medium containing at least 5% by weight quaternary ammonium hydroxide at a high overvoltage cathode.

12. The process of claim 11 in which the electrolysis is conducted on a continuous basis with addition of additional aniline reactant and removal of product by extraction during the electrolysis to keep the product concentration relatively low.

13. The process of claim 11 in which the electrolysis is conducted on a continuous basis with a catholyte having about 10% to about 30% by weight of quaternary ammonium hydroxide, and with extraction of product during the electrolysis by hydrocarbon solvent, keeping the product concentration in the catholyte lower than that of the reactant compound.

14. The process of claim 13 in which the reactant compound is 2-methylsulfinylmethyl-6-trifluoromethylaniline and its concentration in the catholyte is in the range of about 1% to about 10% by weight.

15. The process of claim 1 in which the electrolysis is carried out in a divided cell with an aprotic catholyte and an acidic anolyte, and the cell utilizes a cation exchange membrane which permits the electrolysis current to carry hydrogen protons from the anolyte to the catholyte to counter alkalinity which would otherwise increase progressively in the catholyte.

16. The process of claim 11 in which the medium comprises water and acetonitrile and the product is extracted with an alkane of 5 to 8 carbon atoms.

17. The process of claim 4 in which an orthoaminobenzyl sulfone is electrolyzed in a cell with an anion exchange membrane divider which permits sulfinic acid anion to migrate from the catholyte to the anolyte of the cell, thereby limiting sulfinic acid accumulation in the catholyte.

* * * * *